United States Patent
Swaine, Jr. et al.

(10) Patent No.: US 8,865,192 B2
(45) Date of Patent: *Oct. 21, 2014

(54) FLAVOR OILS WITH REDUCED SULFUR CONTENT AND USE IN ORAL CARE COMPOSITIONS

(75) Inventors: Robert Leslie Swaine, Jr., Glendale, OH (US); Marc Hester, Cincinnati, OH (US); Steve Hoke, West Chester, OH (US); Denise McClenathan, Madeira, OH (US); Niranjan Ramji, Mason, OH (US); Gerhard Norbert Zehentbauer, Okeana, OH (US)

(73) Assignee: The Procter & Gamble Co, Cincinnati, OH (US)

( * ) Notice: Subject to any disclaimer, the term of this patent is extended or adjusted under 35 U.S.C. 154(b) by 960 days.

This patent is subject to a terminal disclaimer.

(21) Appl. No.: 11/825,278

(22) Filed: Jul. 5, 2007

(65) Prior Publication Data

US 2008/0008729 A1  Jan. 10, 2008

Related U.S. Application Data

(60) Provisional application No. 60/819,154, filed on Jul. 7, 2006, provisional application No. 60/819,156, filed on Jul. 7, 2006.

(51) Int. Cl.
| | |
|---|---|
| A61K 8/02 | (2006.01) |
| A61K 8/21 | (2006.01) |
| A61K 8/22 | (2006.01) |
| A61K 8/24 | (2006.01) |
| A23L 1/22 | (2006.01) |
| A61Q 11/00 | (2006.01) |
| A61K 8/34 | (2006.01) |
| A23L 1/222 | (2006.01) |
| A61K 8/33 | (2006.01) |
| A61K 8/19 | (2006.01) |
| A61K 8/35 | (2006.01) |
| A61K 8/92 | (2006.01) |
| A61K 8/49 | (2006.01) |
| A61K 8/67 | (2006.01) |

(52) U.S. Cl.
CPC ............. *A23L 1/222* (2013.01); *A61K 8/347* (2013.01); *A23V 2002/00* (2013.01); *A61K 8/33* (2013.01); *A61K 8/19* (2013.01); *A61K 2800/52* (2013.01); *A61K 8/35* (2013.01); *A61K 8/922* (2013.01); *A61K 8/4973* (2013.01); *A61K 8/676* (2013.01); *A61Q 11/00* (2013.01)
USPC ............. 424/401; 424/48; 424/49; 424/52; 424/53; 424/56; 424/57; 424/58; 426/534

(58) Field of Classification Search
CPC ........ A61K 8/922; A61Q 11/00; A23L 1/222; A23L 1/2225; A23L 1/2215; C11B 9/00
USPC ....................................................... 424/401
See application file for complete search history.

(56) References Cited

U.S. PATENT DOCUMENTS

| | | | |
|---|---|---|---|
| 3,867,262 A |  | 2/1975 | Rockland et al. |
| 4,112,066 A | * | 9/1978 | Hussein .................. 424/48 |
| 4,242,323 A | * | 12/1980 | Vlock ..................... 424/58 |
| 4,335,102 A |  | 6/1982 | Nakashima et al. |
| 4,440,790 A |  | 4/1984 | Blackwell et al. |
| 4,476,142 A |  | 10/1984 | Netherwood et al. |
| 4,490,398 A |  | 12/1984 | Behr et al. |
| 4,613,513 A |  | 9/1986 | Hussein |
| 4,708,880 A |  | 11/1987 | Hussein |

(Continued)

FOREIGN PATENT DOCUMENTS

| | | |
|---|---|---|
| EP | 0062893 | 10/1982 |
| EP | 0113989 | 7/1984 |

(Continued)

OTHER PUBLICATIONS

Takahashi et al., A New Keto-alcohol, (−)-Mintlactone, )+)-isoMintlactone and Minor Components in Peppermint Oil. Agric. Biol. Chem., 44(7), 1535-1543, 1980.*

Derwent abstract of Shimizu, JP 57200321, published Dec. 1982.*

Scott Benn, Potent Odorants in Peppermint an Cornmint Oils Characterized by GC-O and AEDA, *Perfumer & Flavorist*, vol. 23, Sep./Oct. 1998, pp. 5-16, International Mint Symposium, Seattle, Washington, in 1997.

(Continued)

*Primary Examiner* — Kortney L Klinkel

(74) *Attorney, Agent, or Firm* — James E. Oehlenschlager

(57) ABSTRACT

The present invention relates to flavor oils including mint-, fruit- and spice-type flavors that are specially processed to substantially eliminate low-molecular weight sulfur compounds, in particular dimethyl sulfoxide (DMSO), which has been found to be the main precursor of malodorous species such as dimethyl sulfide and methyl mercaptan. These malodorous species are produced via oxidation-reduction reactions involving such sulfur-containing compounds present in flavor oils. A preferred processing method is an aqueous-washing process, which has advantages of being simple, inexpensive and easy to implement while importantly avoiding the problems of typical processes including non-selective removal of desirable components and subjecting the flavor oils to extreme conditions that may destroy other components and result in undesirable changes in flavor or odor character. Other processing methods to selectively remove non-desired components include (1) distillation to remove polar low boiling point components, (2) filtration through adsorbents selective for sulfur compounds, (3) countercurrent extraction and (4) column chromatography. The processing methods may optionally be followed by reengineering to add back desired components that may have been removed or altered during the processing. The specially processed flavor oils are particularly useful in oral care compositions comprising components with chemical reducing capability such as stannous ions, which react with the sulfur-containing compounds to produce malodorous products.

7 Claims, No Drawings

(56) References Cited

U.S. PATENT DOCUMENTS

| | | | |
|---|---|---|---|
| 4,778,691 | A | 10/1988 | Todd et al. |
| 4,861,616 | A | 8/1989 | Spencer |
| 4,948,595 | A | 8/1990 | Patel et al. |
| 5,004,597 | A | 4/1991 | Majeti et al. |
| 5,030,459 | A | 7/1991 | Barcelon et al. |
| 5,041,294 | A | 8/1991 | Patel |
| 5,047,251 | A | 9/1991 | Spencer |
| 5,116,625 | A | 5/1992 | Patel et al. |
| 5,128,154 | A | 7/1992 | Johnson |
| 5,204,128 | A | 4/1993 | Johnson |
| 5,281,410 | A | 1/1994 | Lukacovic et al. |
| 5,298,238 | A | 3/1994 | Hussein et al. |
| 5,372,824 | A | 12/1994 | Record et al. |
| 5,425,962 | A * | 6/1995 | Johnson et al. .................. 426/3 |
| 5,578,293 | A | 11/1996 | Prencipe et al. |
| 5,582,694 | A | 12/1996 | McClelland et al. |
| 6,042,812 | A * | 3/2000 | Sanker et al. .................. 424/49 |
| 6,479,088 | B1 | 11/2002 | Johnson |
| 2007/0053849 | A1 | 3/2007 | Doyle et al. |

FOREIGN PATENT DOCUMENTS

| | | |
|---|---|---|
| EP | 0349186 A2 | 1/1990 |
| GB | 1336511 | 11/1973 |
| JP | 57200321 * | 12/1982 |
| WO | WO9427566 A1 | 12/1994 |
| WO | WO9600014 A1 | 1/1996 |
| WO | WO0135918 | 5/2001 |

OTHER PUBLICATIONS

William Coleman, III, et al, "The Uses of a non-equilibrated solid phase microextraction method to quantitatively determine the off-notes in mint and other essential oils", *Journal of Science of Food and Agriculture*, 2004, pp. 1223-1228, vol. 84, Issue 10.

William Coleman, III, et al, "Semiquantitative Determination of Off-Notes in Mint Oils by Solid Phase Microextraction", *Journal of Chromatographic Science*, vol. 40, Mar. 2002.

David Moyler, et al, Mint Oils: Potential for Standardizing Profiles with Natural Flavoring Substances, *Perfumer & Flavorist*, vol. 23, pp. 37-42, vol. 23, Mar./Apr. 1998, Allured Publishing Corp.

Levy Canova, "The Composition of Scotch Spearmint Oil", Anais da Academia Brasileira de Ciencia, vol. 44(7): pp. 273-277, 1972, V Congresso Internacional De Oleos Essenciais, Rio De Janeiro.

D.R. Dhingra, et al, Peppermint Oil and the Possibility of Its Production in Uttar Pradesh, *Indian Soap Journal*, vol. 17, pp. 43-51, Aug. 1951, H.B. Technological Institute, Kanpur.

O.Johnson and J.C. Snyder, "Peppermint Oil Production in Washington", *Bulletin* 1936, pp. 3-8.

Katsuhiro Takahashi, et al, A New Keto-alcohol, (−) Mintlactone, (+)-*iso*Mintlactone and Minor Components in Peppermint Oil, Agric. Biol. Chem., 44(7), pp. 1535-1543, 1980, Dec. 19, 1979.

Thomas W. Pearson, et al, "Natural Occurring Levels of Dimethyl Sulfoxide in Selected Fruits, Vegetables, Grains, and Beverages", *J. Agric. Food Chem*, 1981, pp. 1089-1091, Jun. 12, 1981.

Chevron Phillips Chemical Company LP, Dimethyl disulfide Material Safety Data revised Jul. 18, 2013.

* cited by examiner

FLAVOR OILS WITH REDUCED SULFUR CONTENT AND USE IN ORAL CARE COMPOSITIONS

CROSS REFERENCE TO RELATED APPLICATION

This application claims the benefit of U.S. Provisional Application Nos. 60/819,154 and 60/819,156, both filed Jul. 7, 2006.

TECHNICAL FIELD

The present invention relates to oral care compositions containing a flavor system comprising flavor oils that are stable against degradation and production of malodor and off-taste and mainly derived from sulfur-containing species such as thiols or mercaptans. These malodorous species are produced via oxidation-reduction reactions involving sulfur-containing compounds present in flavor oils and other components of the composition. The flavor oils are specially processed to reduce the content of low-molecular weight sulfur compounds, in particular dimethyl sulfoxide (DMSO), which has been found to be the main precursor of malodorous species such as dimethyl sulfide and methyl mercaptan. The present invention thus provides methods to produce flavor oils, including mint-, fruit- and spice-type flavors that are substantially free of DMSO and other sulfur-containing species and oral care compositions incorporating such specially processed flavor oils for improved stability in terms of taste and odor profile.

BACKGROUND OF THE INVENTION

Oral care products such as dentifrice and mouthrinse are routinely used by consumers as part of their oral care hygiene regimens. It is well known that oral care products can provide both therapeutic and cosmetic hygiene benefits to consumers. Therapeutic benefits include caries prevention which is typically delivered through the use of various fluoride salts; gingivitis prevention by the use of an antimicrobial agent such as triclosan, stannous fluoride, or essential oils; or hypersensitivity control through the use of ingredients such as strontium chloride or potassium nitrate. Cosmetic benefits provided by oral care products include the control of plaque and calculus formation, removal and prevention of tooth stain, tooth whitening, breath freshening, and overall improvements in mouth feel impression which can be broadly characterized as mouth feel aesthetics. Calculus and plaque along with behavioral and environmental factors lead to formation of dental stains, significantly affecting the aesthetic appearance of teeth. Behavioral and environmental factors that contribute to teeth staining propensity include regular use of coffee, tea, cola or tobacco products, and also the use of certain oral products containing ingredients that promote staining, such as cationic antimicrobials and metal salts.

Thus daily oral care at home requires products with multiple ingredients working by different mechanisms to provide the complete range of therapeutic and aesthetic benefits, including anticaries, antimicrobial, antigingivitis, antiplaque and anticalculus as well as antiodor, mouth refreshment, stain removal, stain control and tooth whitening. In order for oral care products for daily use such as dentifrice and rinses to provide complete oral care it is necessary to combine actives and additives, many of which have the disadvantage of causing negative aesthetics during use, in particular unpleasant taste and sensations and stain promotion. The unpleasant taste and mouth sensations have been described as having one or more of bitter, metallic, astringent, salty, numbing, stinging, burning, prickling, and even irritating aspects. Typical ingredients for oral care use that are associated with these aesthetic negatives include antimicrobial agents such as cetyl pyridinium chloride, chlorhexidine, stannous, copper and zinc salts; tooth bleaching agents such as peroxides; antitartar agents such as pyrophosphate, tripolyphosphate and hexametaphosphate; and excipients such as baking soda and surfactants. To mitigate the aesthetic negatives from these ingredients, oral care products are typically formulated with flavoring agents and sweeteners to taste as good as possible and be consumer acceptable.

Because of the many proven benefits to the oral cavity, stannous ions are desired to be incorporated in oral care compositions. Stannous ions, typically supplied from stannous fluoride in oral care compositions are used to provide benefits including antimicrobial, anti-plaque, antigingivitis and anti-sensitivity and to prevent mouth malodor. However, formulating with stannous ions has proven to be challenging as formulations containing the stannous ions have been known to not be aesthetically pleasing. In addition, it has been found that certain flavoring oils, especially mint-type oils when used in combination with stannous ions can exhibit instability and malodor production.

Refining or further processing of natural flavor oils following extraction from plants or plant materials, to improve quality and stability have been described in the art. Generally these processing methods are aimed at removing or reducing the content in the oils of components believed to be responsible for instability or undesirable taste or odor characteristics. For example, flavor oils have been treated to remove or reduce the content of terpenes, menthofuran, pulegone and dimethyl sulfide. Such treatment processes are described for example in U.S. Pat. Nos. 3,867,262; 4,440,790; 4,613,513; 4,708,880; 4,844,883; 4,816,616; 4,948,595; 5,116,625; 5,128,154; 5,204,128; 5,298,238; 5,425,962; and 6,479,088, and include distillation, nitrogen sparging, and chemical treatment to oxidize or inactivate such undesirable components.

Peppermint oils for example may be distilled to remove or reduce the level of dimethyl sulfide which is reported to provide an undesirable green weedy note. Steam or vacuum distillations have been performed to refine peppermint oil. However, such distillation processes are not entirely satisfactory. The typical steam distillation process in addition to removing dimethyl sulfide also removes other low boiling point peppermint oil components. It is therefore necessary when refining peppermint oil to separate desirable low boiling components from the distillate and add them back at least in part to the flavor. This increases the cost and time of the distillation process. An additional problem with most currently used methods of refining peppermint oil is that they may subject the peppermint oil to extreme conditions, such as excessive heat. This can produce undesirable changes in the flavor.

There continues to be a need for improved processing of flavor oils to provide optimum taste and odor characteristics and stability, in particular to remove malodor-forming components specifically dimethyl sulfoxide, which has now been found to be the major form of malodor-precursor sulfur species in flavor oils. The present invention accordingly involves the removal of such previously unrecognized undesirable odor-forming components from starting flavor oil(s) with production of a stable flavor which is essentially free of undesirable amounts of such malodor-forming components and hence also free of malodor-forming or flavor contaminating tendencies due to reactions with reducing agents such as stannous in oral care compositions.

SUMMARY OF THE INVENTION

In one aspect the present invention is directed to further processing or refining of flavor oils to reduce the content of sulfur-containing compounds, such as dimethyl sulfoxide. A preferred processing method is an aqueous washing process, which has the advantages of being simple, inexpensive and easy to implement while importantly avoiding the problems of typical processes including non-selective removal of desirable components and subjecting the flavor oils to extreme conditions that may destroy other components and result in undesirable changes in flavor and odor character. Other processing methods to selectively remove non-desired components include (1) distillation to remove polar low boiling point components, (2) filtration through adsorbents selective for sulfur compounds, (3) countercurrent extraction and (4) column chrmatography. The processing methods may optionally be followed by reengineering to add back desired components that may have been removed or altered during the processing.

In a further aspect, the invention provides oral care compositions comprising
(a) an oral care agent having chemical reducing capability,
(b) a flavor system comprising flavor oil(s) or extract(s) essentially free of sulfur-containing species including dimethyl sulfoxide, dimethyl sulfide, dimethyl disulfide and dimethyl sulfone, responsible for generation of malodor and off-taste in said compositions, and
(c) an orally-acceptable carrier.

The oral care agent having chemical reducing capability is selected from a stannous ion source and phenolics from sources such as tea, cranberry, pomegranate and oak bark. The compositions have a stable, well-rounded flavor profile and are pleasant tasting and refreshing, thereby encouraging user compliance and frequent use.

These and other features, aspects, and advantages of the present invention will become evident to those skilled in the art from the detailed description which follows.

DETAILED DESCRIPTION OF THE INVENTION

While the specification concludes with claims particularly pointing out and distinctly claiming the invention, it is believed that the present invention will be better understood from the following description.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

Herein, "comprising" means that other steps and other components which do not affect the end result can be added. This term encompasses the terms "consisting of" and "consisting essentially of."

As used herein, the word "include" and its variants, are intended to be non-limiting, such that recitation of items in a list is not to the exclusion of other like items that may also be useful in the materials, compositions, devices, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

By "oral care composition" is meant a product, which in the ordinary course of usage, is not intentionally swallowed for purposes of systemic administration of particular therapeutic agents, but may be retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, denture care product, mouthspray, lozenge, chewable tablet or chewing gum. The oral care composition may also be incorporated onto strips or films for direct application or attachment to oral surfaces.

The term "dentifrice", as used herein, means paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "flavor oils" refers to essential oils used as flavoring agents, which are volatile oils distilled or expressed from plants and constituents of these volatile oils. The term "flavor oils" as used herein when referring to mint and mint-type oils includes various grades of the oil typically referred to as prime natural or unfolded (freshly extracted from plant source) and refined or rectified to standardize the oil and remove unwanted flavor/odor characters (e.g., by fractional distillation). The rectified grade is generally the commercial grade supplied to end users for use as flavorings and perfumes. Typical essential oils and their main constituents are those obtained for example from thyme (thymol, carvacrol), oregano (carvacrol, terpenes), lemon (limonene, terpinene, phellandrene, pinene, citral), lemongrass (citral, methylheptenone, citronellal, geraniol), orange flower (linalool, β-pinene, limonene), orange (limonene, citral), anise (anethole, safrol), clove (eugenol, eugenyl acetate, caryophyllene), rose (geraniol, citronellol), rosemary (borneol, bornyl esters, camphor), geranium (geraniol, citronellol, linalool), lavender (linalyl acetate, linalool), citronella (geraniol, citronellol, citronellal, camphene), eucalyptus (eucalyptol); peppermint (menthol, menthyl esters), spearmint (carvone, limonene, pinene); wintergreen (methyl salicylate), camphor (safrole, acetaldehyde, camphor), bay (eugenol, myrcene, chavicol), cinnamon (cinnamaldehyde, cinnamyl acetate, eugenol), tea tree (terpinen-4-ol, cineole), and cedar leaf (α-thujone, β-thujone, fenchone). Essential oils, their composition and production, are described in detail in Kirk-Othmer *Encyclopedia of Chemical Technology*, 4$^{th}$ Edition and in *The Merck Index*, 13$^{th}$ Edition.

The term "orally acceptable carrier" includes safe and effective materials, excipients or additives used in oral care compositions including but not limited to fluoride ion sources, anti-calculus or anti-tartar agents, buffers, abrasives such as silica, alkali metal bicarbonate salts, thickening materials, humectants, water, surfactants, titanium dioxide, flavoring agents, sweetening agents, xylitol, coloring agents, and mixtures thereof.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed.

Herein, the terms "tartar" and "calculus" are used interchangeably and refer to mineralized dental plaque biofilms.

The essential and optional components of the present compositions are described in the following paragraphs.

Flavor System

The present compositions comprise a flavor system comprising flavor oils that are stable against degradation and production of off-notes and malodor mainly derived from sulfur-containing species such as thiols or mercaptans. These malodorous species are produced via oxidation-reduction reactions involving components of flavor oils and other components of the composition. More specifically, it has now been discovered that low-molecular weight sulfur compounds such as dimethyl sulfoxide (DMSO) are present in certain natural flavor oils in sufficient quantities to react with agents having fairly strong reducing capability, i.e., can be easily oxidized, resulting in production of malodorous species including dimethyl sulfide and methyl mercaptan. The present invention thus provides flavor oils, including mint-, fruit- and spice-type flavors that are specially processed to reduce the content of DMSO and other sulfur-containing species and oral care compositions incorporating such processed flavor oils for improved taste and stability. Preferably the processed flavor oils are essentially free of such undesirable sulfur-containing species including dimethyl sulfoxide, dimethyl sulfide, dimethyl disulfide and dimethyl sulfone that can be reduced to malodorous species. Other sulfur-containing compounds may still be present in the processed oil; however these do not appear to be problematic in terms of malodor generation. By "essentially free" herein is meant that the flavor oil comprises less than about 20 ppm of sulfur-containing species that are malodor precursors. It has been found that formulating flavor oils containing greater than about 20 ppm of such sulfur-containing species with agents such as stannous can result in malodor production that has been described as "skunky". Further, such redox reactions leading to the malodor are disadvantageous in decreasing the concentration of active stannous in the composition, thus potentially decreasing efficacy. Preferably the level of malodor precursor sulfur-containing species in the flavors oils after processing such as by water washing, is less than about 10 ppm, more preferably less than about 1 ppm and even more preferred less than about 0.5 ppm or none at all.

The present invention involves the discovery that the main malodor precursor sulfur-containing species present in flavor oils is DMSO, with samples having levels as high as 300 ppm or more. The following table shows levels of DMSO and dimethyl sulfide (DMS) in spearmint and peppermint samples. As shown below, the main species is DMSO; significantly lower amounts of DMS are found in the flavor oils.

TABLE 1

| DMSO and DMS Levels in Feedstock Peppermint and Spearmint Oils | | |
|---|---|---|
| Sample | DMSO (ppm, w/v) | DMS (ppm, w/v) |
| Peppermint Feedstock Sample 1 | 318 | 10.3 |
| Peppermint Feedstock Sample 2 | 312 | 22.1 |
| Peppermint Feedstock Sample 3 | 181 | 46.8 |
| Spearmint (1% head cut) | 235 | <1 |

Peppermint oils supplied by I.P. Callison, Spearmint oil supplied by Labbeemint

The occurrence of DMSO in nature has been reported. For example, naturally occurring levels of DMSO in selected fruits, vegetables, grains and beverages are reported in *J. Agric. Food Chem.* 1981, 29, pp. 1089-91. The highest level reported was in black tea beverage with 16 ppm. In most samples, the level found was less than 1 ppm, with higher levels found in concentrated or processed samples such as tomato paste. It was thought that the increase in DMSO levels may be due to oxidation of dimethyl sulfide (DMS) during commercial processing. DMS is found extensively in nature and is responsible for the characteristic odor of many foods. DMSO was also reported to occur in spearmint oil [*Anais de Academia Brasileira de Ciencias*, 1972, 44 (Suppl.), 273-7] and in peppermint oil [*Agric. Biol. Chem.*, 1980, 44(7), 1535-43]. There have been no reports of the levels discovered in the mint flavor oils herein.

Determination of the levels of dimethyl sulfoxide (DMSO) and dimethyl sulfide (DMS) in mint oils was achieved via sample dilution followed by liquid injection into a GC-MS system. Briefly, calibration standards were prepared by spiking known quantities of DMSO and DMS into peppermint oil that was previously water washed to remove these components to below the lower limit of quantification. The water washing technique is in accordance with the present invention and described in detail below. Each standard and sample was prepared for analysis by dilution of a 200 μL aliquot with 800 μL of ethyl acetate containing stable-isotope labeled internal standards for DMSO ($^{13}C_2$) and DMS ($^2H_6$). Prepared standards and samples were analyzed by injecting a 1 μL aliquot into a split/splitless inlet of an Agilent 6890 GC. The column effluent was transferred to an Agilent 5973 single quadrupole mass spectrometer, which was operated in selected ion monitoring (SIM) mode. For each analyte, peak area ratios (analyte/internal standard) for the calibration standards were plotted versus spiked analyte concentrations. Each unknown sample concentration was interpolated from the corresponding calibration curve based on its measured analyte to internal standard peak area ratio. Using these assay conditions, the nominal lower limit of quantification for both DMSO and DMS was 1 ppm (w/v) with upper limits for quantification of 500 and 100 ppm for DMSO and DMS, respectively.

The present flavor oils are generally used in oral care compositions at levels of from about 0.001% to about 5%, by weight of the composition. Preferably, the flavor oil is present from about 0.01% to about 4%, more preferably from about 0.05% to about 3%, and most preferably from about 0.1% to about 2%. The flavor oil can be present as the entire flavor composition of an oral formulation or can be combined with other selected flavor ingredients. Preferred flavor oils for use in oral care compositions include those derived from *Mentha* species such as *M. piperita* (peppermint), *M. arvensis* (corn mint), *M. spicata* (U.S. native spearmint), *M. cardiaca* (Scotch spearmint) and *M. viridis Crispa* (spearmint form China). It is desired that the oral care composition has an overall minty taste in that mint is the most dominant flavor therein.

In addition to the select mint flavor oils above, the flavor system may comprise additional flavor ingredients including but not limited to oil of wintergreen, clove bud oil, *cassia*, sage, parsley oil, marjoram, lemon, orange, cis-jasmone, 2,5-dimethyl-4-hydroxy-3(2H)-furanone, 5-ethyl-3-hydroxy-4-methyl-2(5H)-furanone, vanillin, ethyl vanillin, anisaldehyde, 3,4-methylenedioxybenzaldehyde, 3,4-dimethoxybenzaldehyde, 4-hydroxybenzaldehyde, 2-methoxybenzaldehyde, benzaldehyde; cinnamaldehyde, hexyl cinnamaldehyde, alpha-methyl cinnamaldehyde, ortho-methoxy cinnamaldehyde, alpha-amyl cinnamaldehydepropenyl guaethol, heliotropine, 4-cis-heptenal, diacetyl, methyl-p-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, anethole, dihydroanethole, carvone, menthone, β-damascenone, ionone, gamma decalactone, gamma nonalactone, and gamma undecalactone and mixtures thereof. Generally suitable flavoring ingredients are those containing structural features and functional groups that are less prone to redox reactions. These include derivatives of flavor chemicals that are saturated or contain stable aromatic rings or ester groups. Also suitable are flavor chemicals that may undergo some oxidation or degradation without resulting in a significant change in the flavor character or profile. The flavor ingredients may be provided as single or purified chemicals or supplied in the composition by addition of natural oils or extracts that have preferably undergone the present water-washing treatment or other refining to remove components that are relatively unstable and may degrade and alter the desired flavor profile, resulting in a less acceptable product from an organoleptic standpoint.

The flavor system may also include a protectant component that prevents generation of off odor and off taste in the composition such as described in co-filed copending application entitled FLAVORS FOR ORAL COMPOSITIONS. Such protectants include carbonyl compounds such as ascorbic acid; cis-jasmone; 2,5-dimethyl-4-hydroxy-3(2H)-furanone; 5-ethyl-3-hydroxy-4-methyl-2(5H)-furanone; vanillin; ethyl vanillin; anisaldehyde; 3,4-methylenedioxybenzaldehyde; 3,4-dimethoxybenzaldehyde; 4-hydroxybenzaldehyde; 2-methyoxybenzaldehyde; 4-methoxybenzaldehyde; benzaldehyde; cinnamaldehyde; hexyl cinnamaldehyde; alpha-methyl cinnamaldehyde; ortho-methoxy cinnamaldehyde; alpha-amyl cinnamaldehyde; and combinations thereof. Many of these protectants are flavor ingredients.

The flavor system may further comprise cooling agents or coolants such as menthol, menthyl esters, carboxamides, ketals, diols, and mixtures thereof. Examples of suitable coolants useful in the present compositions are the paramenthan carboxamide agents such as N-ethyl-p-menthan-3-carboxamide, known commercially as "WS-3"; N,2,3-trimethyl-2-isopropylbutanamide, known as "WS-23"; N-ρ-benzeneacetonitrile-menthanecarboxamide; and others in the series such as WS-5, WS-11, WS-14 and WS-30. Additional suitable coolants include 3-1-menthoxypropane-1,2-diol known as TK-10 manufactured by Takasago; menthone glycerol acetal (Frescolat® MGA); menthyl esters such as menthyl acetate, menthyl acetoacetate, menthyl lactate (Frescolat® ML supplied by Haarmann and Reimer), and monomenthyl succinate (under the tradename Physcool from V. Mane). The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

The flavor system will typically include a sweetening agent. Suitable sweeteners include those well known in the art, including both natural and artificial sweeteners. Some suitable water-soluble sweeteners include monosaccharides, disaccharides, polysaccharides and derivatives such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, xylitol and erythritol. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, and the like. Water-soluble sweeteners derived from naturally occurring water-soluble sweeteners, such as a chlorinated derivative of ordinary sugar (sucrose), known, for example, under the product description of sucralose as well as protein based sweeteners such as *thaumatococus danielli* (Thaumatin I and II) can be used. The composition preferably contains from about 0.1% to about 10% of sweetener, preferably from about 0.1% to about 1%, by weight.

In addition the flavor system may include salivating agents, warming agents, and numbing agents. These agents are present in the compositions at a level of from about 0.001% to about 10%, preferably from about 0.1% to about 1%, by weight of the composition. Suitable salivating agents include Jambu® manufactured by Takasago. Examples of warming agents are *capsicum* and nicotinate esters, such as benzyl nicotinate. Suitable numbing agents include benzocaine, lidocaine, clove bud oil, and ethanol.

Chemical Reducing Agents

The flavor system comprising the present specially processed flavor oils and extracts are particularly useful in compositions comprising agents that have chemical reducing capability, in particular stannous ions which as described above is a preferred active in oral care compositions because of its wide range of benefits and phenolics and derivatives derived from plant sources with useful antimicrobial, anti-inflammatory and antioxidant activities. Many of these phenolics and derivatives are also useful as flavoring agents.

Stannous ions have fairly strong reducing properties, being oxidized to stannic form when reacting with DMSO which in turn is reduced to the malodor species DMS and further to methyl mercaptan ($CH_3SH$). The reaction of stannous with agents such as DMSO is undesirable not only because of the production of malodorous species but also in decreasing the level of stannous and thus the efficacy of the composition.

Many of the phenolics used in oral care compositions as actives or flavor agents are susceptible to oxidation, i.e., have reducing capability and can thus react with DMSO in the same manner as stannous.

The present compositions preferably include a stannous ion source, including stannous fluoride and/or other stannous salts. Stannous fluoride has been found to help in the reduction of caries, gingivitis, plaque and sensitivity, and in improved breath benefits. Other stannous salts include stannous chloride dihydrate, stannous acetate, stannous gluconate, stannous oxalate, stannous sulfate, stannous lactate, and stannous tartrate. The preferred stannous ion sources are stannous fluoride and stannous chloride dihydrate. The stannous salt(s) will be present in an amount of from about 0.1% to about 11%, by weight of the total composition. Preferably, the stannous salts are present in an amount of from about 0.4% to about 7%, more preferably from about 0.45% to about 5%, and most preferably from about 0.45% to about 3% by weight of the total composition. Formulations providing efficacy typically include stannous levels, provided by stannous fluoride and other stannous salts, ranging from about 3,000 ppm to about 15,000 ppm stannous ions in the total composition.

Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients needed to stabilize the stannous may be included, such as the ingredients described in Majeti et al. and Prencipe et al.

Phenolics from plant sources such as tea, cranberry, pomegranate and oak bark may also be incorporated in the present compositions. Such phenolics include catechin, gallocatechin gallate, epicatechin (EC), epigallocatechin (EGC), epigallocatechin gallate (EGCG), epicatechin gallate (ECG), theaflavine, thearubigins, anthocyanidins/proanthocyanidins and anthocyanins (e.g., cyanidin, delphinidin, pelargonidin, peonidin, malvidin and petunidin); tannic acid; gallic acid; ellagic acid; ellagitannins; curcumin. The phenolics may be supplied as purified compounds or as plant extracts. Phenolics useful as oral care actives are disclosed in commonly assigned U.S. patent application Ser. No. 11/595,530, published as US 2007/0053849A1.

In addition to the components described above, the present compositions may comprise additional optional components collectively referred to as orally acceptable carrier materials, which are described in the following paragraphs.

Orally Acceptable Carrier Materials

The orally acceptable carrier comprises one or more compatible solid or liquid excipients or diluents which are suitable for topical oral administration. By "compatible," as used herein, is meant that the components of the composition are capable of being comingled without interaction in a manner which would substantially reduce the composition's stability and/or efficacy.

The carriers or excipients of the present invention can include the usual and conventional components of dentifrices, non-abrasive gels, subgingival gels, mouthwashes or rinses, mouth sprays, chewing gums, lozenges and breath mints as more fully described hereinafter.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, etc. as disclosed in e.g., U.S. Pat. No. 3,988,433 to Benedict. Carrier materials for biphasic dentifrice formulations are disclosed in U.S. Pat. No. 5,213,790, issued May 23, 1993; U.S. Pat. No. 5,145,666, issued Sep. 8, 1992; and U.S. Pat. No. 5,281,410 issued Jan. 25, 1994 all to Lukacovic et al. and in U.S. Pat. Nos. 4,849, 213 and 4,528,180 to Schaeffer. Mouthwash, rinse or mouth spray carrier materials typically include water, flavoring and sweetening agents, etc., as disclosed in, e.g., U.S. Pat. No. 3,988,433 to Benedict. Lozenge carrier materials typically include a candy base; chewing gum carrier materials include a gum base, flavoring and sweetening agents, as in, e.g., U.S. Pat. No. 4,083,955 to Grabenstetter et al. Sachet carrier materials typically include a sachet bag, flavoring and sweetening agents. For subgingival gels used for delivery of actives into the periodontal pockets or around the periodontal pockets, a "subgingival gel carrier" is chosen as disclosed in, e.g. U.S. Pat. Nos. 5,198,220 and 5,242,910, issued Mar. 30, 1993 and Sep. 7, 1993, respectively both to Damani. Carriers suitable for the preparation of compositions of the present invention are well known in the art. Their selection will depend on secondary considerations like taste, cost, and shelf stability, etc.

The compositions of the present invention may also be in the form of non-abrasive gels and subgingival gels, which may be aqueous or non-aqueous. In still another aspect, the invention provides a dental implement impregnated with the present composition. The dental implement comprises an implement for contact with teeth and other tissues in the oral cavity, said implement being impregnated with the present composition. The dental implement can be impregnated fibers including dental floss or tape, chips, strips, films and polymer fibers.

In one embodiment, the compositions of the subject invention are in the form of dentifrices, such as toothpastes, tooth gels and tooth powders. Components of such toothpaste and tooth gels generally include one or more of a dental abrasive (from about 6% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion) and an anticalculus agent (from about 0.1% to about 13%). Tooth powders, of course, contain substantially all non-liquid components.

Other embodiments of the subject invention are liquid products, including mouthwashes or rinses, mouth sprays, dental solutions and irrigation fluids. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion) and an anticalculus agent (from about 0.1% to about 3%). Components of dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Types of orally acceptable carriers or excipients which may be included in compositions of the present invention, along with specific non-limiting examples, are discussed in the following paragraphs.

Tooth Substantive Agent

The present invention may include a tooth substantive agent such as polymeric surface active agents (PMSA's), which are polyelectrolytes, more specifically anionic polymers. The PMSA's contain anionic groups, e.g., phosphate, phosphonate, carboxy, or mixtures thereof, and thus, have the capability to interact with cationic or positively charged entities. The "mineral" descriptor is intended to convey that the surface activity or substantivity of the polymer is toward mineral surfaces such as calcium phosphate minerals or teeth.

PMSA's are useful in the present compositions because of their stain prevention benefit. It is believed the PMSA's provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSA's on teeth can also prevent stains from accruing due to disruption of binding sites of color bodies on tooth surfaces.

The ability of PMSA's to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers.

The desired surface effects include: 1) creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

The polymeric mineral surface active agents include any agent which will have a strong affinity for the tooth surface, deposit a polymer layer or coating on the tooth surface and produce the desired surface modification effects. Suitable examples of such polymers are polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); polycarboxylates and carboxy-substituted polymers; and mixtures thereof. Suitable polymeric mineral surface active agents include the carboxy-substituted alcohol polymers described in U.S. Pat. Nos. 5,292,501; 5,213,789; 5,093,170; 5,009,882; and 4,939,284; all to Degenhardt et al. and the diphosphonate-derivatized polymers in U.S. Pat. No. 5,011,913 to Benedict et al; the synthetic anionic polymers including polyacrylates and copolymers of maleic anhydride or acid and methyl vinyl ether (e.g., Gantrez), as described, for example, in U.S. Pat. No. 4,627,977, to Gaffar et al. A preferred polymer is diphosphonate modified polyacrylic acid. Polymers with activity must have sufficient surface binding propensity to desorb pellicle proteins and remain affixed to enamel surfaces. For tooth surfaces, polymers with end or side chain phosphate or phosphonate functions are preferred although other polymers with mineral binding activity may prove effective depending upon adsorption affinity.

Additional examples of suitable phosphonate containing polymeric mineral surface active agents include the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakikhani et al. and U.S. Pat. No. 6,071,434 to Davis et al. Additional polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other suitable polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsaturated C=C bonds (e.g., acrylate and methacrylate monomers), such as those having the following structure:

1. Co-telomer of acrylic acid and 2-(hydroxyphosphinyl)ethylidene-1,1-diphosphonic acid with structure:

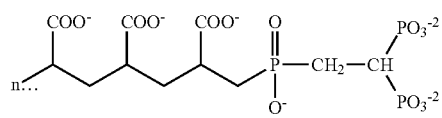

2. Co-polymer of acrylic acid and vinyldiphosphonic acid with structure:

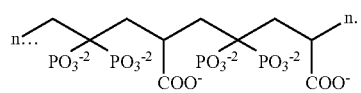

Suitable polymers include the diphosphonate/acrylate polymers supplied by Rhodia under the designation ITC 1087 (Average MW 3000-60,000) and Polymer 1154 (Average MW 6000-55,000).

A preferred PMSA will be stable with other components of the oral care composition such as ionic fluoride and metal ions. Also preferred are polymers that have limited hydrolysis in high water content formulations, thus permitting a simple single phase dentifrice or mouthrinse formulation. If the PMSA does not have these stability properties, one option is a dual phase formulation with the polymeric mineral surface active agent separated from the fluoride or other incompatible component. Another option is to formulate non-aqueous, essentially non-aqueous or limited water compositions to minimize reaction between the PMSA and other components.

A preferred PMSA is a polyphosphate. A polyphosphate is generally understood to consist of two or more phosphate molecules arranged primarily in a linear configuration, although some cyclic derivatives may be present. Although pyrophosphates (n=2) are technically polyphosphates, the polyphosphates desired are those having around three or more phosphate groups so that surface adsorption at effective concentrations produces sufficient non-bound phosphate functions, which enhance the anionic surface charge as well as hydrophilic character of the surfaces. The inorganic polyphosphate salts desired include tripolyphosphate, tetrapolyphosphate and hexametaphosphate, among others. Polyphosphates larger than tetrapolyphosphate usually occur as amorphous glassy materials. Preferred in this invention are the linear polyphosphates having the formula:

$$XO(XPO_3)_nX$$

wherein X is sodium, potassium or ammonium and n averages from about 3 to about 125. Preferred polyphosphates are those having n averaging from about 6 to about 21: such as those commercially known as Sodaphos (n=6), Hexaphos (n=13), and Glass H (n=21) and manufactured by FMC Corporation and Astaris. These polyphosphates may be used alone or in combination. Polyphosphates are susceptible to hydrolysis in high water formulations at acid pH, particularly below pH 5. Thus it is preferred to use longer-chain polyphosphates, in particular Glass H with an average chain length of about 21. It is believed such longer-chain polyphosphates when undergoing hydrolysis produce shorter-chain polyphosphates which are still effective to deposit onto teeth and provide a stain preventive benefit.

Other polyphosphorylated compounds may be used in addition to or instead of the polyphosphate, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds.

The amount of tooth substantive agent will typically be from about 0.1% to about 35% by weight of the total oral composition. In dentifrice formulations, the amount is preferably from about 2% to about 30%, more preferably from about 5% to about 25%, and most preferably from about 6% to about 20%. In mouthrinse compositions, the amount of tooth substantive agent is preferably from about 0.1% to 5% and more preferably from about 0.5% to about 3%.

In addition to creating the surface modifying effects, the tooth substantive agent may also function to solubilize insoluble salts. For example, Glass H polyphosphate has been found to solubilize insoluble stannous salts. Thus, in compositions containing stannous salts for example, Glass H contributes to decreasing the stain promoting effect of stannous.

Fluoride Source

It is common to have a water-soluble fluoride compound present in dentifrices and other oral compositions in an amount sufficient to give a fluoride ion concentration in the composition, and/or when it is used of from about 0.0025% to about 5.0% by weight, preferably from about 0.005% to about 2.0% by weight, to provide anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al. Representative fluoride ion sources include: stannous fluoride, sodium fluoride, potassium fluoride, sodium monofluorophosphate, indium fluoride and many others. Stannous fluoride and sodium fluoride are preferred, as well as mixtures thereof.

Abrasives

Dental abrasives useful in the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxies, and cross-linked polyesters.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Examples include the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in Wason, U.S. Pat. No. 4,340,583, issued Jul. 29, 1982; and in commonly-assigned U.S. Pat. No. 5,603,920, issued on Feb. 18, 1997; U.S. Pat. No. 5,589,160, issued Dec. 31, 1996; U.S. Pat. No. 5,658,553, issued Aug. 19, 1997; 5,651,958, issued Jul. 29, 1997, and U.S. Pat. No. 6,740,311, issued May 25, 2004.

Mixtures of abrasives can be used such as mixtures of the various grades of Zeodent® silica abrasives listed above. The total amount of abrasive in dentifrice compositions of the subject invention typically range from about 6% to about 70% by weight; toothpastes preferably contain from about 10% to about 50% of abrasives, by weight of the composition. Dental solution, mouth spray, mouthwash and non-abrasive gel compositions of the subject invention typically contain little or no abrasive.

Anticalculus Agent

The present compositions may optionally include an additional anticalculus agent, such as a pyrophosphate salt as a source of pyrophosphate ion. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, from about 1.5% to about 10% in one embodiment, and from about 2% to about 6% in another embodiment. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is a preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in *Kirk-Othmer Encyclopedia of Chemical Technology*, 3rd Edition, Volume 17, Wiley-Interscience Publishers (1982).

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al., as well as, e.g., polyamino propane sulfonic acid (AMPS), diphosphonates (e.g., EHDP; AHP), polypeptides (such as polyaspartic and polyglutamic acids), and mixtures thereof.

Chelating Agents

Another optional agent is a chelating agent, also called sequestrants, such as gluconic acid, tartaric acid, citric acid and pharmaceutically-acceptable salts thereof. Chelating agents are able to complex calcium found in the cell walls of the bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention. Suitable chelating agents will generally have a calcium binding constant of about $10^1$ to $10^5$ to provide improved cleaning with reduced plaque and calculus formation. Chelating agents also have the ability to complex with metallic ions and thus aid in preventing their adverse effects on the stability or appearance of products. Chelation of ions, such as iron or copper, helps retard oxidative deterioration of finished products.

Examples of suitable chelating agents are sodium or potassium gluconate and citrate; citric acid/alkali metal citrate combination; disodium tartrate; dipotassium tartrate; sodium potassium tartrate; sodium hydrogen tartrate; potassium hydrogen tartrate; sodium, potassium or ammonium polyphosphates and mixtures thereof. The amounts of chelating agent suitable for use in the present invention are about 0.1% to about 2.5%, preferably from about 0.5% to about 2.5% and more preferably from about 1.0% to about 2.5%.

Still other chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Examples are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether; polyacrylic, polyitaconic and polymaleic acids; and sulfoacrylic oligomers of M.W. as low as 1,000 available as Uniroyal ND-2.

Other Active Agents

The present invention may optionally include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, and triclosan monophosphate. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. Pat. No. 4,206,215, issued Jun. 3, 1980, to Bailey. Other antimicrobials such as copper salts, zinc salts and stannous salts may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Preferred antimicrobial agents include zinc salts, stannous salts, cetyl pyridinium chloride, chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. These agents provide anti-plaque benefits and are typically present at levels of from about 0.01% to about 5.0%, by weight of the composition.

Another optional active agent that may be added to the present compositions is a dentinal desensitizing agent to control hypersensitivity, such as salts of potassium, calcium, strontium and tin including nitrate, chloride, fluoride, phosphates, pyrophosphate, polyphosphate, citrate, oxalate and sulfate.

Peroxide Source

The present compositions may contain a peroxide source for its many benefits to the oral cavity. It has long been recognized that hydrogen peroxide and other peroxygen-containing agents are effective in curative and/or prophylactic treatments with respect to caries, dental plaque, gingivitis, periodontitis, mouth odor, tooth stains, recurrent aphthous ulcers, denture irritations, orthodontic appliance lesions, postextraction and postperiodontal surgery, traumatic oral lesions and mucosal infections, herpetic stomatitis and the like. Peroxide-containing agents in the oral cavity exert a chemomechanical action generating thousands of tiny oxygen bubbles produced by interaction with tissue and salivary enzymes. The swishing action of a mouthrinse enhances this inherent chemomechanical action. Such action has been recommended for delivery of other agents into infected gingival crevices. Peroxide mouthrinses prevent colonization and multiplication of anaerobic bacteria known to be associated with periodontal disease.

Peroxide sources include peroxide compounds, perborates, percarbonates, peroxyacids, persulfates, and combinations thereof. Suitable peroxide compounds include hydrogen peroxide, urea peroxide, calcium peroxide, sodium peroxide, zinc peroxide and mixtures thereof. A preferred percarbonate is sodium percarbonate. Preferred persulfates are oxones. Preferred peroxide sources for use in dentifrice formulations include calcium peroxide and urea peroxide. Hydrogen peroxide and urea peroxide are preferred for use in mouthrinse formulations. The following amounts represent the amount of peroxide raw material, although the peroxide source may contain ingredients other than the peroxide raw material. The present composition may contain from about 0.01% to about 30%, preferably from about 0.1% to about 10%, and more preferably from about 0.5% to about 5% of a peroxide source, by weight of the composition.

Surfactants

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. The present composition typically comprises an anionic surfactant at a level of from about 0.025% to about 9%, from about 0.05% to about 5% in some embodiments, and from about 0.1% to about 1% in other embodiments.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate. The sarcosinate surfactant may be present in the compositions of the present invention from about 0.1% to about 2.5%, preferably from about 0.5% to about 2.0% by weight of the total composition.

Cationic surfactants useful in the present invention include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., where said quaternary ammonium fluorides have detergent properties. Certain cationic surfactants can also act as germicides in the compositions disclosed herein. Cationic surfactants such as chlorhexidine, although suitable for use in the current invention, are not preferred due to their capacity to stain the oral cavity's hard tissues. Persons skilled in the art are aware of this possibility and should incorporate cationic surfactants with this limitation in mind.

Nonionic surfactants that can be used in the compositions of the present invention include compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Zwitterionic synthetic surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Suitable betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N,N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice include cocoamidopropyl betaines and preferably, the lauramidopropyl betaine.

Thickening Agents

In preparing toothpaste or gels, thickening agents are added to provide a desirable consistency to the composition, to provide desirable active release characteristics upon use, to provide shelf stability, and to provide stability of the composition, etc. Suitable thickening agents include one or a combination of carboxyvinyl polymers, carrageenan, hydroxyethyl cellulose (HEC), natural and synthetic clays (e.g., Veegum and laponite) and water soluble salts of cellulose ethers such as sodium carboxymethylcellulose (CMC) and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Suitable carboxyvinyl polymers useful as thickening or gelling agents include carbomers which are homopolymers of acrylic acid crosslinked with an alkyl ether of pentaerythritol or an alkyl ether of sucrose. Carbomers are commercially available from B.F. Goodrich as the Carbopol® series, including Carbopol 934, 940, 941, 956, and mixtures thereof.

Thickening agents are typically present in an amount from about 0.1% to about 15%, preferably from about 2% to about 10%, more preferably from about 4% to about 8%, by weight of the total toothpaste or gel composition, can be used. Higher concentrations may be used for chewing gums, lozenges and breath mints, sachets, non-abrasive gels and subgingival gels.

Humectants

Another optional carrier material of the present compositions is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, propylene glycol and trimethyl glycine.

Miscellaneous Carrier Materials

Water employed in the preparation of commercially suitable oral compositions should preferably be of low ion content and free of organic impurities. Water may comprise up to about 99% by weight of the aqueous compositions herein. These amounts of water include the free water which is added plus that which is introduced with other materials, such as with sorbitol.

The present invention may also include an alkali metal bicarbonate salt, which may serve a number of functions including abrasive, deodorant, buffering and adjusting pH. Alkali metal bicarbonate salts are soluble in water and unless stabilized, tend to release carbon dioxide in an aqueous system. Sodium bicarbonate, also known as baking soda, is a commonly used alkali metal bicarbonate salt. The present composition may contain from about 0.5% to about 30%, preferably from about 0.5% to about 15%, and most preferably from about 0.5% to about 5% of an alkali metal bicarbonate salt.

The pH of the present compositions may be adjusted through the use of buffering agents. Buffering agents, as used herein, refer to agents that can be used to adjust the pH of aqueous compositions such as mouthrinses and dental solutions preferably to a range of about pH 4.0 to about pH 6.0 for peroxide stability. Buffering agents include sodium bicarbonate, monosodium phosphate, trisodium phosphate, sodium hydroxide, sodium carbonate, sodium acid pyrophosphate, citric acid, and sodium citrate. Buffering agents are typically included at a level of from about 0.5% to about 10%, by weight of the present compositions.

Poloxamers may be employed in the present compositions. A poloxamer is classified as a nonionic surfactant and may also function as an emulsifying agent, binder, stabilizer, and other related functions. Poloxamers are difunctional blockpolymers terminating in primary hydroxyl groups with molecular weights ranging from 1,000 to above 15,000. Poloxamers are sold under the tradename of Pluronics and Pluraflo by BASF. Suitable poloxamers for this invention are Poloxamer 407 and Pluraflo LA370.

Other emulsifying agents that may be used in the present compositions include polymeric emulsifiers such as the Pemulen® series available from B.F. Goodrich, and which are predominantly high molecular weight polyacrylic acid polymers useful as emulsifiers for hydrophobic substances.

Titanium dioxide may also be added to the present composition. Titanium dioxide is a white powder which adds opacity to the compositions. Titanium dioxide generally comprises from about 0.25% to about 5% by weight of dentifrice compositions.

Other optional agents that may be used in the present compositions include dimethicone copolyols selected from alkyl- and alkoxy-dimethicone copolyols, such as $C_{12}$ to $C_{20}$ alkyl dimethicone copolyols and mixtures thereof. Highly preferred is cetyl dimethicone copolyol marketed under the trade name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits.

Removal of Malodor-Forming Components of Flavor Oils

A further aspect of the present invention is a refining or clean-up treatment to remove or significantly reduce the level of undesirable sulfur-containing species in flavor oils and extracts to prepare what is referred to herein as "select" flavor oils.

Aqueous Wash Process

A preferred cleanup treatment is an aqueous washing process which is simple, inexpensive, and easily implementable in large scale. The aqueous medium may be all water or a water-solvent mixture with the solvent comprising about 20% or less. The method for eliminating the undesirable components generally involves their extraction from the flavor oil into the aqueous phase. DMSO and dimethyl sulfone are highly polar and freely soluble in water and other solvents such as alcohol. These compounds can easily be extracted from the oil with plain water or a water-alcohol mixture. The use of a co-solvent such as alcohol may improve the removal of less polar species such as DMS. The co-solvent may be any food-grade water-miscible solvent such as ethanol, isopropanol, glycerin and propylene glycol, which will extract undesirable species such as DMS without significantly extracting desirable components from the oil. The pH of the aqueous medium can generally be in the range about 3 to about 12, preferably about 7 or neutral. The exact preference in pH will depend upon the pH stability of the flavor oil being processed. The aqueous medium may optionally contain salts, which may be helpful in "salting out" most of the flavor components from the aqueous phase and keeping them in the flavor oil itself. Flavor oil samples are mixed with the aqueous medium at a water:oil volume ratio ranging from about 90:10 to about 10:90, preferably from about 70:30 to about 30:70. In general the more the water the faster the rate of removal of DMSO; however too much water may lead to emulsion and render final separation of the oil phase from the water phase difficult. Regular water may be used; USP grade water is preferred. The process is typically conducted at room temperature conditions. Again, the choice of temperature conditions is dependent on the temperature stability of the flavor oil.

The water and oil phases are subjected to stirring or vigorous mixing conditions for better water and oil contact producing a turbid mixture. Mixing of the oil and water phases is continued for about 30 minutes up to 3 hours or longer. Depending on the mixing conditions and batch size sufficient cleanup or extraction can be achieved in about 30 minutes, i.e., the level of sulfur compounds remaining in the oil has been reduced to the target level. After mixing is stopped, the phases are allowed to separate and the oil phase is then separated from the water phase. The separated oil phase may then be subjected to additional water washes with fresh water each time and/or filtration through a hydrophilic/hydrophobic adsorbent material to remove any remaining turbidity in the oil. The washed oil may also be subjected to centrifugation or cooling to achieve separation of water left in the washed oil. The level of DMSO and other sulfur-containing compounds in the oil phase is quantified at certain intervals to determine if additional agitation/mixing or washing steps are necessary.

Improved mixing and contact of the flavor oil and water can be achieved using high shear mixers to achieve DMSO removal over a shorter period of time. Mixers that can be used include high shear mixers such as Ross Mixers for batch mixing or online mixing. Examples of suitable batch mixers include a High speed Disperser (typically used for 1 gallon-1000 gallon batches) consisting of a vertical shaft and a high shear disc type blade. The blade rotates at up to about 10,000 RPM and creates a flow pattern within a stationary mix vessel. The blade creates a vortex that pulls in the contents of the vessel to the blades sharp edge. The blade then mechanically breaks the oil phase and disperses it in the water phase. Another batch mixer model is the High Shear Rotor-Stator mixer design consisting of a single stage rotor that turns at high speed within a stationary stator. As the rotating blades pass the stator, they mechanically shear the oil water phase. Small lab scale mixers have a speed of mixing of 500-10,000 RPM (for 0.3-15 L capacity of liquid). Larger commercial scale mixers have speeds of 3600-1200 RPM (for Rotor diameters of 64 mm-330 mm) for a 15 L-22,710 L capacity of liquid. An example of Ultra High Shear Online mixer is a Ross model s that has a four stage or greater rotors that turn at a speed of 15000 feet per minute within a stationary stator. As the rotating blades pass the stator, they mechanically shear the contents.

In an example, 250 ml of Peppermint oil was taken in a 2 L glass beaker. To it was added 150 mil of USP water and stirred with a magnetic stirrer vigorously until the oil and water formed a turbid mixture. The stirring was continued at room temperature. At about 0.5 hr, 1 hr and 2 hr intervals, the stirring was stopped to allow the phases to separate. Within a few minutes the phases separated and a 1 ml sample of the oil was taken for analysis. After 2 hours mixing, the phases were allowed to separate and the upper oil layer was decanted and allowed to stand in a glass bottle for 24-48 hrs to further clarify the small amount of turbidity remaining in the oil. The oil was then filtered through 0.45 um Hydrophilic PVDF filter (Millipore) to clarify the oil and stored in glass jar until used.

The above procedure was applied to unfolded peppermint oil feedstock (supplied by I. P. Callison) and the DMSO levels in the oil phase are as follows. DMSO was quantified using GC-MSD. As the results show, after about a half hour of water washing, greater than 95% of the DMSO has been removed from the oil with less than 1 ppm remaining after 2 hours.

| Sample | DMSO (ppm, w/v) |
|---|---|
| Peppermint Oil Feedstock # 1 | 307 |
| 35 min. washed Feedstock | 12.7 |
| 60 min. washed Feedstock | 16.5 |
| 2 hr. washed Feedstock | <1 |

In addition to DMSO, the aqueous washing treatment removes other water soluble compounds in the oils such as low molecular weight alcohols and aldehydes as well as less water-soluble compounds such as dimethyl sulfide (DMS). However, the removal of DMS proceeds at a somewhat slower rate compared to DMSO. It is believed that as the water phase solubilizes DMSO and other organic compounds, the water phase becomes less polar, creating a better medium for removal of DMS and other compounds of similar polarity and solubility characteristics.

In another example, the compounds removed from a sample mint oil subjected to the present water washing process were determined. A rectified peppermint oil sample supplied by I. P. Callison was subjected to water washing for 5 hours followed by an additional 7 hour washing step with fresh water. Each washing step was performed with a 1:1 water to oil mixture with gentle stirring. Mint oil from both before and after this washing procedure was analyzed by SPME GC-MS and the approximate reduction of each component was estimated by comparing the resulting chromatograms. A partial list of compounds whose concentrations were reduced by the washing procedure is provided in Table 2 below. There is reasonably good correlation between percent compound removed and Log P (octanol/water partition coefficient). The correlation is even better when considering the molecular weight of each compound. Importantly, the concentrations of the relatively non-polar, major components in peppermint oil are not significantly changed by the water washing procedure. These major components include menthol, menthone, alpha- and beta-pinene, limonene, etc.

TABLE 2

Compounds Removed by Water Washing Peppermint Oil

| Compound Number | Compound Reduced | ~% Reduction |
|---|---|---|
| 1 | Methanol | 95 |
| 2 | Methyl formate | 95 |
| 3 | Ethanol | 95 |
| 4 | Acetone | 65 |
| 5 | Furan | 90 |
| 6 | Formic acid ethyl ester | 90 |
| 7 | Acetic acid methyl ester | 85 |
| 8 | Dimethyl sulfide | 99+ |
| 9 | Carbon disulfide | 90 |
| 10 | 2-Methyl propanal | 60 |
| 11 | Acetic acid | 70 |
| 12 | 2-Butanone | 70 |
| 13 | 2-Methyl furan | 70 |

TABLE 2-continued

Compounds Removed by Water Washing Peppermint Oil

| Compound Number | Compound Reduced | ~% Reduction |
|---|---|---|
| 14 | 3-Methyl furan | 70 |
| 15 | 2-Methyl-1-propanol | 40 |
| 16 | Crotonaldehyde | 60 |
| 17 | 3-Methyl butanal | 50 |
| 18 | 2-Methyl butanal | 50 |
| 19 | 2-Pentanone | 35 |
| 20 | Cyclopentanol | 35 |
| 21 | 2-Ethyl furan | 20 |
| 22 | 2-Methyl-1-butanol | 15 |
| 23 | 2-Methyl crotonaldehyde | 30 |
| 24 | Dimethyl disulfide | 40 |
| 25 | 3-Methyl crotonaldehyde | 30 |
| 26 | Hexanal | 15 |
| 27 | Dimethyl sulfoxide | 99+ |
| 28 | Furfural | 35 |
| 29 | 2-Hexenal | 15 |
| 30 | 2,5-Diethyl THF | 5 |

The washed or select peppermint oil was compared to traditional rectified oil in terms of odor characteristics. Washed peppermint oil and unwashed rectified peppermint oils were odor evaluated by a panel of trained flavorists, using a 0-100 scale, where 0 was a poor grade of oil and 100 was an excellent quality of oil. The average ratings were 33 for the unwashed oil and 67 for the washed oil, indicating the washed oil is superior to the unwashed rectified oil.

A typical peppermint predominant finished flavor oil for a dentifrice, containing 62% of either a rectified peppermint oil or a washed peppermint oil was evaluated by the same expert flavor panel, using the same scale. The average grade for the unwashed rectified oil was 58 and 75 for the washed oil, indicating the washed oil to be of superior quality.

A dentifrice containing 0.454% stannous fluoride was prepared and flavored with either rectified peppermint oil or washed peppermint oil. The dentifrices were stored at 40 C for a period of 3 months. During this period the dentifrice with the washed oil did not develop any off odor while the unwashed rectified oil did develop an off odor. Evaluations were conducted by trained flavorists using a 0 (no off odor) to 10 (intense off odor) scale for presence and intensity of malodor during the storage period. Scores assigned to the dentifrice samples are as follows. These evaluations demonstrate the stability of the water washed oils in the presence of a reducing agent such as stannous.

| | Months of Storage | | |
|---|---|---|---|
| | 1 | 2 | 3 |
| Dentifrice w/ Unwashed Rectified Oil | 3 | 7 | 7 |
| Dentifrice w/ Washed Rectified Oil | 0 | 0 | 0 |

These series of experiments demonstrate that the water washing process can be used to stabilize rectified flavor oils as well as prime natural or crude flavor oils that have not gone through a refining or rectification treatment. Advantageously the water washing process is simple, efficient and economical and avoids thermal abuse of the flavor oil. The process may be sufficient to prepare commercial grade flavor oils without need for more complicated rectification processes.

Filtration Process

Another technique that may be used to remove DMSO and other sulfur compounds from flavor oils is filtration using materials selective for sulfur compounds. Such filtration materials include commercially available materials useful as adsorbents and molecular sieves. Examples include the following materials supplied by the Engelhard Corporation and Johnson Matthey Catalysts.

a) SELEXSORB CDX—a composition of Aluminum Oxide Hydrate (60-85% w/w %) and Alumino Silicate (15-40% w/w), density—42.2 cu.ft, surface area 431 sq M/g, size 7×14 mesh.

b) SELEXSORB COS—a composition of Aluminum Oxide Hydrate (88-99% w/w %) and Alkali metal Oxide (1-5% w/w %), density—49.8 cu.ft., surface area 255 sq M/g, size 7×14 mesh.

c) Catalyst CP367—Nickel/nickel oxide on an inert support d) Catalyst CP366—A mixture of basic copper carbonate, basic zinc carbonate and aluminum oxide.

In an example, rectified peppermint oil supplied by I. P Callison was subjected to filtration using the above materials as adsorbent. The adsorbent material (60 g) was packed in a stainless steel column (from Millipore, 3.5 cm diameter×30 cm length) fitted with a filter pad at the bottom of the column (Isopore membrane filter from Millipore, 2 um TTTP filter). 150 ml of peppermint oil was poured on top of the column bed and the oil which passed through the column under gravity feed was collected at the bottom. The first 75 ml of the oil was collected (designated as $1^{st}$ cut) followed by the second 75 ml (designated as $2^{nd}$ cut). The filtered oil was analyzed for DMSO by the method described earlier. Results are summarized below.

TABLE 3

DMSO Removal from Peppermint Oil by Filtration

| | Sample | DMSO (ppm, w/v) | % Removed |
|---|---|---|---|
| 1 | Rectified Peppermint Oil | 197 | — |
| 2 | Selexsorb COS $1^{st}$ cut | 173 | 12 |
| 3 | Selexsorb COS $2^{nd}$ cut | 130 | 34 |
| 4 | Selexsorb CDX $1^{st}$ cut | 66 | 66 |
| 5 | Selexsorb CDX $2^{nd}$ cut | 7.4 | 96 |
| 6 | CP 366 $1^{st}$ cut | 173 | 12 |
| 7 | CP 366 $2^{nd}$ cut | 138 | 30 |
| 8 | CP 367 $1^{st}$ cut | 142 | 28 |
| 9 | CP 367 $2^{nd}$ cut | 130 | 34 |

Countercurrent Extraction (CCE)

The technique of countercurrent extraction (CCE) may be also used to remove non-desired components from flavor oils. This technique has been used in the flavor industry to manufacture deterpenated oils. In the original patented process essential oils are deterpenated by a double solvent extraction process using a polar and a nonpolar solvent. The essential oil goes through a mixing chamber and agitated with a countercurrent flow of the two solvents, resulting in continuous extraction of the terpenes into the polar solvent. In a variation of the original CCE process, citrus oil is partitioned by pumping the citrus oil against a flow of hydroalcoholic solvent being pumped in the opposite direction. The terpenes are extracted from the citrus oil by the hydroalcoholic solvent. Similarly, the CCE technique may be used to extract DMSO and other sulfur compounds using water as the extractant. The CCE technique is discussed in R. L. Swaine, "Flavoring Agents" in *Food Additive Toxicology* (1995), Maga & Tu (eds,).

Distillation

Flavor oils may also be fractionated using standard distillation and/or extraction techniques to remove the non-desired components. This can be carried out through standard distillation procedures such as using a vacuum distillation apparatus or a spinning band column. The final flavor oil can be reengineered or produced by selecting which components are desired and combining the components. For example, in mint oils, particularly those derived from a *Mentha* or *Mentha*-like source such as peppermint oil, over 225 volatile compounds have been identified so far. However, it is also established that only a very limited number among the pool of volatile components actually make a substantial contribution to the overall odor of a product. Therefore, effective screening methods are needed to separate the most odor-active compounds from the bulk of volatiles compounds exhibiting little or no odor. It is preferred to include as many components commonly found in natural mint oils as possible to provide a full, well balanced minty taste without any off-taste or malodor. If a less selective fractionation or refining of the mint oil is done and more components are removed and not added back, the resulting mint oil flavor composition may not be as desirable. Therefore, it is desired to selectively fractionate the mint oil to provide the most aesthetically pleasing mint flavor.

Mint oils including those commonly known as peppermint, spearmint, and corn mint may be fractionated by distillation to remove volatile (lower boiling point) polar compounds, which are undesirable, specifically DMSO and other sulfur-containing compounds such as sulfides and disulfides. The polar, lower boiling point components may have boiling points less than about 12° C., less than about 14° C., less than about 16° C. or even less than about 18° C. The distillation process would also remove other low molecular weight compounds such as $C_3$-$C_9$ aldehydes and alcohols.

The fractionated or select mint oil would be essentially free of low boiling, polar compounds including DMSO and dimethyl sulfide. Other components that are removed or significantly reduced include branched alkanals such as 2-methylpropanal, 2-methyl butanal, and 3-methyl butanal; branched alkanols such as 2-methylpropanol, 2-methylbutanol, and 3-methylbutanol; alkenols such as Z-3-hexenol; alkenals such as E-2-hexenal; other aldehydes, alcohols and ketones such as 3-methyl cyclohexanone, benzaldehyde, 1-octen-3-ol, 3-octanone, and 2,3-dehydro-1,8-cineole. Specific components that the select mint oil may include are α-pinene, β-pinene, sabinene, mycrene, α-phellandrene, α-terpinene, limonene, cis-ocimeme, eucalyptol, trans-ocimene, γ-terpiene, 3-octanol, terpineolene, sabinene hydrate, linalool, menthofuran, isopulegol, menthone, neomenthol, terpien-4-ol, isomenthone, menthol, neoisomenthol, isomenthol, α-terpineol, pulegone, menthyl acetate, carvone, neoisomenthyl acetate, piperitone, b-bourbonene, β-caryophyllene, thymol, trans-1-farnesene, α-humulene, germacrene B, elemol, viridiflorol, eucalyptol, γ-terpinene, 1-octanol, n-amyl isovalerate, 1-methyl-4-(1-methylethyl)-trans-2-cyclohexen-1-ol, 1-terpineol, α-terpineol, 4,7-dimethyl-benzofuran, citronellol, neomenthyl acetate, eugenol, ylangene, α-copaene, longifolene, α-gurjunene, caryophyllene, (+)-epi-bicyclosesquiphellendrene, trans-β-farnesene, β-caryophyllene, alloaromadendrene, γ-murrolene, germacrene D, bicyclogermacrene, 8-cadiene, and terpinolene.

Method of Use

The present invention also relates to methods for cleaning teeth and preventing undesirable oral cavity conditions including caries, microbial infection, plaque, calculus, stain and oral malodor and dental erosion.

The method of use herein comprises contacting a subject's dental enamel surfaces and oral mucosa with the oral compositions according to the present invention. The method of use may be by brushing with a dentifrice, rinsing with a dentifrice slurry or mouthrinse, or chewing a gum product. Other methods include contacting the topical oral gel, mouthspray, or other form with the subject's teeth and oral mucosa. The subject may be any person or animal whose tooth surface contact the oral composition. By animal is meant to include household pets or other domestic animals, or animals kept in captivity.

For example, a method of treatment may include a person brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions. The composition is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Major components of select mint oils of the present invention are shown below.

Example I

| Component | % | % |
| --- | --- | --- |
| α-Pinene | 0.63 | 0.19 |
| β-Pinene | 0.90 | 0.23 |
| Sabinene | 0.03 | 0.01 |
| Myrcene | 0.03 | 0.01 |
| α-Terpinene | 0.01 | 0.01 |
| Limonene | 0.50 | 0.05 |
| cis-Ocimene | 0.01 | 0.01 |
| Eucalyptol | 2.64 | 4.71 |
| trans-Ocimene | 0.01 | 0.01 |
| γ-Terpinene | 0.01 | 0.01 |
| 3-Octanol | 0.05 | 0.05 |
| Terpineolene | 0.01 | 0.00 |
| Sabinene Hydrate | 0.04 | 0.34 |
| Linalool | 0.07 | 0.59 |
| Menthofuran | 0.14 | 2.16 |
| Isopulegol | 0.02 | 0.02 |
| Menthone | 16.89 | 2.27 |
| Neomenthol | 2.22 | 0.86 |
| Terpinen-4-ol | 0.03 | 0.04 |
| Isomenthone | 3.56 | 0.40 |
| Menthol | 66.42 | 73.87 |
| Isomenthol | 0.04 | 0.14 |
| α-Terpineol | 0.35 | 0.58 |
| Pulegone | 0.14 | 0.04 |
| Menthyl Acetate | 3.53 | 5.95 |
| Neoisomenthyl Acetate | 0.01 | 0.00 |
| Piperitone | 0.06 | 1.35 |
| β-Bourbonene | 0.02 | |
| β-Caryophyllene | 0.11 | 3.12 |
| Thymol | 0.03 | 0.02 |
| trans-β-Farnesene | 0.08 | 0.01 |
| α-Humulene | 0.02 | 0.24 |
| Germacrene D | 0.32 | 0.05 |
| Triacetin | | 0.17 |
| Germacrene B | | 0.08 |

-continued

| Component | % | % |
|---|---|---|
| Elemol | | 0.89 |
| Viridiflorol | 0.03 | 0.03 |
| Menthalactone | | 0.17 |

Flavor compositions containing select mint oils processed according to the present invention are shown below. The select mint oils are essentially free of DMSO and other malodor precursor sulfur compounds. The flavor compositions containing the present mint oils are judged in organoleptic testing to be aesthetically pleasing and can be incorporated in oral care compositions containing reducing agents such as stannous and tea polyphenols without developing off odors or taste.

Example II

| Ingredient | % |
|---|---|
| Select mint oil | 60% |
| Anethole | 10% |
| Menthol | 25% |
| Eucalyptol | 5% |

Example III

| Ingredient | % |
|---|---|
| Select peppermint oil | 42% |
| Select spearmint oil | 5% |
| WS-3 coolant | 10% |
| Anethole | 7% |
| Menthol | 35% |
| Aloe | 1% |

Oral compositions containing stannous ions, select mint oils in the flavor composition, and orally acceptable carriers are shown below with amounts of ingredients in weight %. These compositions are made using conventional methods. Example 1V illustrates dual phase dentifrice compositions; the first and second phases may be packaged in physically separated compartments of a dispenser and dispensed side-by-side typically at a 50:50 ratio. Example V illustrates single phase dentifrice compositions.

Example IV

| First Dentifrice Composition | | Second Dentifrice Composition | |
|---|---|---|---|
| Ingredient | Wt. % | Ingredient | Wt. % |
| Carboxymethycellulose | 0.500 | Sodium Hydroxide[b] | 1.000 |
| Water | 2.768 | Color | 0.300 |
| Flavor | 1.000 | Water | 21.840 |
| Glycerin | 36.432 | Flavor | 1.000 |
| Polyethylene Glycol | 1.500 | Glycerin | 28.992 |
| Propylene Glycol | 8.000 | Sodium Gluconate | 4.160 |
| Sodium Lauryl Sulfate[a] | 4.000 | Stannous Chloride | 3.000 |
| Silica | 28.000 | Silica | 23.000 |
| Benzoic Acid | 0.600 | Sodium Saccharin | 0.300 |
| Sodium Benzoate | 0.600 | Poloxamer | 15.500 |
| Sodium Saccharin | 0.300 | Stannous Fluoride | 0.908 |
| Titanium Dioxide | 1.000 | | |
| Xanthan Gum | 0.300 | | |
| Glass H Polyphosphate | 15.000 | | |

[a] 27.9% solution
[b] 50% solution

Example V

| Ingredient | IVA | IVB | IVC | IVD | IVE | IVF | IVG |
|---|---|---|---|---|---|---|---|
| Phytic Acid (20% Soln) | 4.000 | 2.000 | | | 10.000 | | |
| Na Phytate (20% Soln.) | | | 10.000 | 4.000 | | | |
| Zn Carbonate[1] | 2.000 | 1.000 | | 2.000 | | | |
| Zn Oxide | | | 5.000 | | | | |
| Zn Pyrophosphate | | | | | | 8.000 | |
| Zn Lactate | | | | | | 2.500 | |
| Na Polyphosphate | | | | | | 13.000 | |
| Stannous Fluoride | 0.454 | 0.454 | | 0.454 | | 0.454 | 0.454 |
| Sodium Fluoride | | | 0.243 | | 0.243 | | |
| Stannous Chloride | | | 1.500 | | 1.000 | | 1.500 |
| Tea Extract | | | | 2.000 | | | |
| EGCG | | | | | | 1.000 | 1.000 |
| Sodium Gluconate | 0.672 | 0.600 | 0.672 | 0.600 | 0.672 | 0.652 | 2.100 |
| Sorbitol Soln | 34.275 | 35.785 | 34.275 | 35.785 | 34.275 | | 37.496 |
| Glycerin | | | | | | 38.519 | 14.425 |
| HEC | 0.300 | 0.300 | 0.300 | 0.300 | 0.300 | | |
| Na CMC | 1.200 | 1.300 | 1.200 | 1.300 | 1.200 | | 0.600 |
| Carrageenan | 0.500 | 0.500 | 0.500 | 0.500 | 0.500 | 0.600 | |
| Xanthan Gum | | | | | | 0.350 | 0.700 |
| PEG | | | | | | 7.000 | |
| Propylene Glycol | | | | | | 7.000 | |
| Silica Abrasive | 20.000 | 16.000 | 20.000 | 16.000 | 20.000 | 25.000 | 20.000 |
| TiO$_2$ (Anatase) | 0.525 | 0.525 | 0.525 | 0.525 | 0.525 | | 0.525 |
| SLS (28% Soln.) | 4.000 | 7.500 | 4.000 | 7.500 | 4.000 | 2.500 | 5.000 |
| Na Saccharin | 0.250 | 0.250 | 0.250 | 0.250 | 0.250 | 0.500 | 0.300 |
| Flavor | 0.950 | 0.950 | 0.950 | 0.950 | 0.950 | 0.800 | 1.000 |
| NaOH | 0.006 | 0.122 | 0.006 | 0.122 | 0.006 | | 0.600 |

-continued

| Ingredient | IVA | IVB | IVC | IVD | IVE | IVF | IVG |
|---|---|---|---|---|---|---|---|
| Na Phosphate Tribasic | | | | | | 1.100 | |
| Water and Minors, e.g., Color soln. | QS | QS | QS | QS | QS | QS | QS |

[1]Zinc Carbonate AC supplied by Bruggemann Chemical: Newtown Square, PA, USA

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A flavor composition for use in oral care products comprising one or more flavor oil(s) or extract(s) wherein the one or more flavor oil(s) or extract(s) comprise no more than 1 ppm by weight dimethyl sulfoxide (DMSO) that is a precursor for generation of malodor and off-taste in said composition or products, and wherein the one or more flavor oil(s) or extract(s) is derived from peppermint, corn mint, spearmint or a mixture thereof, and wherein the one or more flavor oil(s) or extract(s) are subjected to a process consisting essentially of one or a combination of a washing process the flavor oil(s) or extract with an aqueous phase comprising water and no more than about 20% of solvent and filtration through an adsorbent material comprising a metal oxide to substantially eliminate dimethyl sulfoxide.

2. The flavor composition of claim 1 comprising one or more additional flavoring agents selected from oil of wintergreen, clove bud oil, cassia, sage, parsley oil, marjoram, lemon, orange, cis-jasmone, 2,5-dimethyl-4-hydroxy-3(2H)-furanone, 5-ethyl-3-hydroxy-4-methyl-2(5H)-furanone, vanillin, ethyl vanillin, anisaldehyde, 3,4-methylenedioxybenzaldehyde, 3,4-dimethoxybenzaldehyde, 4-hydroxybenzaldehyde, 2-methoxybenzaldehyde, benzaldehyde; cinnamaldehyde, hexyl cinnamaldehyde, α-methyl cinnamaldehyde, ortho-methoxy cinnamaldehyde, α-amyl cinnamaldehydepropenyl guaethol, heliotropine, 4-cis-heptenal, diacetyl, methyl-p-tert-butyl phenyl acetate, menthol, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, anethole, dihydroanethole, carvone, menthone, β-damascenone, ionone, γ-decalactone, γ-nonalactone, and γ-undecalactone.

3. An oral care product comprising
   (a) an oral care agent having chemical reducing capability selected from a stannous ion source and phenolics from sources selected from tea, cranberry, pomegranate and oak bark,
   (b) a flavor system comprising flavor oil(s) or extract(s) comprising no more than 1 ppm by weight dimethyl sulfoxide that is a precursor for generation of malodor and off-taste and wherein the flavor oil(s) or extract(s) are derived from peppermint, corn mint, spearmint or a mixture thereof, and
   (c) an orally-acceptable carrier.

4. The oral care product of claim 3 in a form selected from a dentifrice, tooth gel, subgingival gel, mouthrinse, mouthspray, mousse, foam, denture care product, lozenge, chewable tablet, chewing gum and strip for direct attachment to teeth.

5. The oral care product of claim 4 which is a dentifrice comprising one or more carrier materials selected from fluoride ion sources, anti-calculus agents, abrasives, desensitizing agents, tooth substantive agents, and additional flavoring agents.

6. The oral care product of claim 5 wherein the tooth substantive agent is selected from polyphosphates having an average chain length of about 3 or more and phytates.

7. The oral care product of claim 3 wherein the stannous ion source comprises one or a mixture of stannous salts selected from stannous fluoride, stannous chloride, stannous chloride dihydrate, stannous acetate, stannous gluconate, stannous oxalate, stannous sulfate, stannous lactate, and stannous tartrate.

* * * * *